United States Patent
Wu et al.

(10) Patent No.: US 11,732,309 B2
(45) Date of Patent: Aug. 22, 2023

(54) IDENTIFICATION OF WHITE LEGHORNS RED PLUMAGE MUTAGENIC MUTANT GENOTYPE AND CULTIVATION METHOD FOR SUPPORTING SYSTEM OF RED PLUMAGE PINK SHELL LAYER CHICKENS

(71) Applicant: Beijing Huadu Yukou Poultry Industry Co., Ltd., Beijing (CN)

(72) Inventors: Guiqin Wu, Beijing (CN); Ning Yang, Beijing (CN); Hao Sun, Beijing (CN); Guangqi Li, Beijing (CN); Congjiao Sun, Beijing (CN); Huani Li, Beijing (CN); Aiqiao Liu, Beijing (CN)

(73) Assignee: BEIJING HUADU YUKOU POULTRY INDUSTRY CO., LTD., Beijing (CN)

( * ) Notice: Subject to any disclaimer, the term of this patent is extended or adjusted under 35 U.S.C. 154(b) by 359 days.

(21) Appl. No.: 16/958,233

(22) PCT Filed: Sep. 27, 2018

(86) PCT No.: PCT/CN2018/107801
§ 371 (c)(1),
(2) Date: Sep. 22, 2020

(87) PCT Pub. No.: WO2019/128350
PCT Pub. Date: Jul. 4, 2019

(65) Prior Publication Data
US 2021/0007334 A1    Jan. 14, 2021

(30) Foreign Application Priority Data
Dec. 29, 2017  (CN) .......................... 201711489025.2

(51) Int. Cl.
C12Q 1/6888    (2018.01)
A01K 67/02     (2006.01)
C12Q 1/683     (2018.01)
C12N 9/22      (2006.01)
C12Q 1/6806    (2018.01)

(52) U.S. Cl.
CPC ............ *C12Q 1/6888* (2013.01); *A01K 67/02* (2013.01); *C12N 9/22* (2013.01); *C12Q 1/683* (2013.01); *C12Q 1/6806* (2013.01); *C12Q 2531/113* (2013.01); *C12Q 2600/124* (2013.01); *C12Q 2600/156* (2013.01)

(58) Field of Classification Search
None
See application file for complete search history.

(56) References Cited

FOREIGN PATENT DOCUMENTS

| | | |
|---|---|---|
| CN | 103898102 A | 7/2014 |
| CN | 104273094 A | 1/2015 |
| CN | 104711339 A | 6/2015 |
| CN | 106520996 A | 3/2017 |
| CN | 108085400 A | 5/2018 |
| CN | 108192981 A | 6/2018 |

OTHER PUBLICATIONS

Ling et al. Association of feather colour with constitutively active melanocortin 1 receptors in chicken. Eur. J. Biochem. 270:1441-1449. (Year: 2003).*
Davila et al. Association between polymorphism in the melanocortin 1 receptor gene and E locus plumage color phenotype. Poultry Science 93:1089-1096. (Year: 2014).*
Guo et al. Genetic variation of chicken MC1R gene in different plumage colour populations. British Poultry Science 51(6): 734-739. (Year: 2010).*
Kerje et al. Melanocortin 1-receptor (MC1R) mutations are associated with plumage colour in chicken. Animal Genetics 34: 241-248. (Year: 2003).*
Takeuchi et al. A possible involvement of melanocortin 1-receptor in regulating feather color pigmentation in the chicken. Biochimica et Biophysica Acta 1308: 164-168. (Year: 1996).*
Hoque, M. R. et al. "Investigation of MC1R SNPs and Their Relationships with Plumage Colors in Korean Native Chicken" Asian Australas. J. Anim. Sci., vol. 26, No. 5, May 31, 2013 (May 31, 2013), pp. 625-629.
Yeo, J. S. et al. "Detection of Exonic Variants Within The Melanocortin 1 Receptor (MC1R) Gene in Black Silky, White Leghorn and Golden Duckwing Araucana Chicken" Mol.Biol.Rep., vol. 41, May 16, 2014 (May 16, 2014), pp. 4843-4846.
Zadinova, K. et al. "Association Analysis of Snps in the Porcine CYP2E1 Gene With Skatole, Indole, and Rostenone Levels in Backfat of a Crossbred Pig Population" Meat Science, vol. 131, Apr. 29, 2017 (Apr. 29, 2017),pp. 68-73.

(Continued)

*Primary Examiner* — Samuel C Woolwine
(74) *Attorney, Agent, or Firm* — Cantor Colburn LLP

(57) ABSTRACT

The present invention discloses a method for breeding the commercial strains of red feather pink-shell laying hens. It provides a primer pair for identifying the red feather causative mutation homozygous genotype of white leghorn chickens, which is composed of the single-stranded DNA molecule shown in Sequence 2 of the Sequence List and the single-stranded DNA molecule shown in Sequence 3 of the list. After the primer was designed according to the upstream and downstream nucleotide sequences of the 18,288,303$^{rd}$ deoxynucleotide in the positive-sense strand of the 11$^{th}$ chromosome as shown in the sequence information of the chicken reference genome Gallus_gallus-4.0 version published in NCBI, the genotype (SNP) at this site is tested through the restriction fragment length polymorphism, the genotype of the site (SNP) was tested through the restriction fragment length polymorphism; the offspring hens obtained by cross breeding the homogenous female parent (the homogenous female parent was obtained through expanded propagation of the white leghorn chickens with the red feather causative mutation homozygous genotype) and the Rhode Island Red rooster as a male parent are all of red feather phenotype, meeting the market demands and enjoying a broad prospect for promotion.

10 Claims, 1 Drawing Sheet

Specification includes a Sequence Listing.

(56) References Cited

OTHER PUBLICATIONS

International Search Report Issued in PCT/CN2018/1077801 dated Dec. 29, 2018.
Teng Zhaochun, Lu Xiaoping, Wang Yuxiang, Jin Deping, Yang Kaimei, Song Minyan, Shi Xianwei. The correlation between MC1R gene Taq?PCR-RFLP marker and taliu black-bone chicken feather color traits[J]. China National Poultry, 2013, 35(20 ): 11-14.
SS185226173, DBSNP Fasta Sequence.
Gunnarsson et al. "Mutations in SLC45A2 cause plumage color variation in chicken and Japanese quail" Genetics 175.2 (Feb. 2007): pp. 867-877.
Kerje et al. "The Dominant white, Dun and Smoky color variants in chicken are associated with insertion/deletion polymorphisms in the PMEL17 gene" Genetics 168.3 (Nov. 2004): pp. 1507-1518.
Office Action issued in Chinese Patent Application No. 201711489025. 2; Application Filing Date Dec. 29, 2017; dated Nov. 28, 2018 (17 pages).
Search Report issued in European Patent Application No. 18893435. 0; Application Filing Date Sep. 27, 2018; dated Jun. 14, 2021 (10 pages).

\* cited by examiner

SEQUENCE LISTING

```
<160> NUMBER OF SEQ ID NOS: 3

<210> SEQ ID NO 1
<211> LENGTH: 288
<212> TYPE: DNA
<213> ORGANISM: Artificial Sequence
<220> FEATURE:
<223> OTHER INFORMATION: original source Gallus Gallus

<400> SEQUENCE: 1
gccgccatcc tcaagaacag gaatctgcac tcgcccatgt actacttcat ctgctgcctg      60
gccgtctccg acatgctggt gagcgtcagc aacctggccg agacgctctt catgctgctg     120
atggagcacg gcgtgctggt gatccgcgcc agcatcgtcc gccacatgga caatgtcatc     180
gacatgctca tctgcagctc cgtcgtgtcc tccctctcct tcctgggggt catcgccgtg     240
gaccgctaca tcacgatctt ctatgcgctg cgttttttttt tttttttt                  28
```

```
<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
gccgccatcc tcaagaaca                                                  19

<210> SEQ ID NO 3
<211> LENGTH: 34
<212> TYPE: DNA
<213> ORGANISM: Artificial Sequence
<220> FEATURE:
<223> OTHER INFORMATION: Primer

<400> SEQUENCE: 3
aaaaaaaaaa aaaaacgcag cgcatagaag atcg                                 34
```

IDENTIFICATION OF WHITE LEGHORNS RED PLUMAGE MUTAGENIC MUTANT GENOTYPE AND CULTIVATION METHOD FOR SUPPORTING SYSTEM OF RED PLUMAGE PINK SHELL LAYER CHICKENS

CROSS REFERENCE TO RELATED APPLICATIONS

This application is a U.S. National Stage entry under 35 U.S.C. § 371 based on International Patent Application No. PCT/CN2018/107801, filed on Sep. 27, 2018, which claims priority to and benefit of Chinese Patent Application No. 201711489025.2, filed Dec. 29, 2017. The contents of which are hereby incorporated herein by reference in their entirety.

FIELD OF THE INVENTION

The invention relates to molecular biology and poultry breeding technology, in particular to a method for identifying the red feather causative mutation genotypes in white leghorn chickens and breeding of commercial strains for red feather pink-shell laying hens.

SEQUENCE LISTING

The instant application contains a Sequence Listing which has been submitted in ASCII format via EFS-WEB and is hereby incorporated by reference in its entirety. Said ASCII copy, created on Sep. 16, 2020, is named 196344-00002_ST25.txt and is 1,313 bytes in size.

BACKGROUND OF THE INVENTION

China is a country traditionally famous for its cuisines. Chinese consumers' demands for eggs have obvious regional characteristics, so their demands for laying hen breeds are also diversified and regionalized. With the improvement of living standards, consumers' demands for eggs do not only focus on the inner quality of eggs but also egg size and egg shell color. The demands for eggs can be roughly divided into four types, namely luxury consumption demand, high-end consumption demand, mass consumption demand and egg processing demand. Pink-shell laying hen breeds have become the "new favorite" in residents' egg consumption due to their small egg weight and large yolk-albumen ratios. According to statistics, the proportion of pink-shell eggs in the market has continued to rise in recent years, to 40%. Meanwhile, the feather color traits of chickens have always been a major indicator for the selection of domestic high-quality chicken breeds and an important trait affecting the economic value of chickens. Due to China's long history and Chinese people's unique consumption concept, red feather laying hens are very popular. It is found in production that some white leghorn chickens have gene mutations in feather color. The cross-breeding of this breed, as the female parent, and the Rhode Island Red chicken, as the male parent, can produce red feather offspring hens. The test cross method is adopted in traditional breeding. This method is to screen out the white leghorn chickens carrying red feather causative mutations according to the feather color phenotypes of the hybrid offspring hens. It is cumbersome, requires plenty of manpower, material and financial resources, and its accuracy cannot reach 100% due to the limitation of extended group size. From the perspective of the supply-side structural reform to follow the new trends in national egg consumption, it is quite necessary to identify the genotypes of feather color causative mutation sites using the molecular detection method, thereby applying the method to breed new commercial strains of domestic laying hens that can lay red feather pink-shell eggs.

SUMMARY OF THE INVENTION

The first purpose of the present invention is to provide the primer pair for red feather causative mutation genotypes of white leghorn chickens.

The primer pair provided by the present invention is composed of the single-stranded DNA molecule shown in SEQ ID NO: 2 of the Sequence List and the single-stranded DNA molecule shown in SEQ ID NO: 3 of the Sequence List.

The second purpose of the present invention is to provide a kit for red feather causative mutation genotypes of white leghorn chickens.

The kit provided by the present invention includes the above primer pair and restriction endonuclease;

The restriction endonuclease is NruI.

The application of the said primer pair or kit in identifying the red feather causative mutation genotypes of white leghorn chickens to be tested also falls within the protection scope of the present invention.

The application of the said primer pair or kit in the breeding of white leghorn chickens with red feather causative mutation homozygous genotypes or red feather causative mutations heterozygous genotypes falls within the protection scope of the present invention as well; or the application of the said primer pair or kit in the breeding of the white leghorn chickens whose offspring hens are produced through cross-breeding of the chickens with Rhode Island Red roosters also falls within the scope of the present invention; or the application of the said primer pair or kit in identifying the red feather traits of the hybrid offspring hens of the white leghorn chickens to be tested and Rhode Island Red roosters; or the application of the said primer pair or kit in the establishment of commercial strains of red feather pink-shell laying hens further falls within the scope of the present invention.

The said red feather causative mutation genotypes of white leghorn chickens to be tested include red-feather causative mutation homozygous and heterozygous genotypes.

The third purpose of the present invention is to provide a method for identifying the red feather causative mutation genotypes in the white leghorn chickens to be tested.

The method provided by the present invention is achieved through the following steps:

1) Perform PCR amplification on the chickens to be tested with the said primer to obtain the PCR amplification product;

2) Digest the said PCR amplification product with the said restriction endonuclease to obtain the digestion product;

3) Test the digestion product, and identify the red feather causative mutation genotypes of the white leghorn chickens to be tested according to the size of the digestion product; or the present invention also provides a method for identifying the red feather traits of the hybrid offspring hens of the white leghorn chickens to be tested and Rhode Island Red roosters, which can be achieved through the following steps:

1) Perform PCR amplification on the chickens to be tested with the said primer to obtain the PCR amplification product;

2) Digest the said PCR amplification product with the said restriction endonuclease to obtain the digestion product;

3) Test the digestion product, and identify the red feather traits of the hybrid offspring hens of the white leghorn chickens to be tested and Rhode Island Red roosters.

In the above method,

The red feather causative mutation genotypes of the white leghorn chickens to be tested are as follows:

If the size of the digestion product of the white leghorn chickens to be tested is only 253 bp, then such chickens are the ones with the red feather causative mutation homozygous genotype;

If the size of the digestion product of the white leghorn chickens to be tested is only 288 bp, then such chickens are the ones without red feather causative mutation; or If the size of the digestion product of the white leghorn chickens to be tested is 288 bp and 253 bp, then such chickens are the ones with the red feather causative mutation heterozygous genotype.

Or, the red feather traits of the hybrid offspring hens of the white leghorn chickens to be tested and the Rhode Island Red roosters according to the size of the digestion product are as follows:

If the size of the digestion product of the white leghorn chickens to be tested is only 253 bp, then the hybrid offspring hens of such white leghorn chickens as female parents and the Rhode Island Red roosters as male parents are all the ones with red feather traits;

If the size of the digestion product of the white leghorn chickens to be tested is only 288 bp, then the hybrid offspring hens of such white leghorn chickens as female parents and the Rhode Island Red roosters as male parents are all the ones without red feather traits;

If the size of the digestion product of the white leghorn chickens to be tested is 288 bp and 253 bp, then the hybrid offspring hens of such white leghorn chickens as female parents and the Rhode Island Red roosters as male parents include the ones with the red feather causative mutation heterozygous genotype and the ones without red feather traits;

In the above method, the template of the said PCR amplification is the genomic DNA of the chickens to be tested.

The fourth purpose of the present invention is to provide a method for breeding the white leghorn chickens with the red feather causative mutation homozygous genotype.

The present invention provides a method for breeding the white leghorn chickens with the red feather causative mutation homozygous genotype, which includes the following step: breeding the white leghorn chickens with the red feather causative mutation homozygous genotype; or the present invention provides a method for breeding the white leghorn chickens to be tested whose offspring hens were hens obtained through hybridization with Rhode Island Red roosters have red feathers, which includes the following step: breeding the white leghorn chickens with the red feather causative mutation homozygous genotype.

The fifth purpose of the present invention is to provide a method for breeding commercial strains of red feather pink-shell laying hens.

The method provided by the present invention includes the following steps:

1) Breeding the said white leghorn chickens with the red feather causative mutation homozygous genotype;

2) Cross breeding the white leghorn chickens with the red feather causative mutation homozygous genotype as the female parent, and the Rhode Island Red roosters as a male parent. All the produced offspring hens have red feathers, and all the little offspring roosters have no red feathers, thereby obtaining the commercial strains of red feather pink-shell laying hens.

The said white leghorn chickens to be tested are the white leghorn breed of Beijing Huadu Yukou Poultry Industry Co., Ltd, including roosters and/or hens.

The experiments of the present invention prove that, after the primer was designed according to the upstream and downstream nucleotide sequences of the $18,288,303^{rd}$ deoxynucleotide in the positive-sense strand of the $11^{th}$ chromosome, as shown in the sequence information of the chicken reference genome Gallus_gallus-4.0 version published in NCBI, the genotype of the site (SNP) was tested through the restriction fragment length polymorphism; 100% of the offspring hens obtained by cross breeding the homogenous female parent (the homogenous female parent was obtained through expanded propagation of the white leghorn chickens with the red feather causative mutation homozygous genotype) and the Rhode Island Red rooster as a male parent are all of red feather phenotype, meeting the market demands and enjoying a broad prospect for promotion. Besides, the use of the restriction fragment length polymorphism test method avoids the tedious test cross breeding, shortens the generation interval, speeds up the breeding process, reduces the breeding cost, and overcomes other shortcomings in the conventional breeding. Furthermore, the method of the present invention can be used to directly identify the genotype of the site of red feather causative mutation of roosters and hens, thus solving the problem that the conventional test crossing method cannot be used to judge the red feather genotypes of roosters, increasing the accuracy and speed for rooster geno-typing and improving the use value of roosters as well.

DETAILED DESCRIPTION OF THE INVENTION

Figure 1:
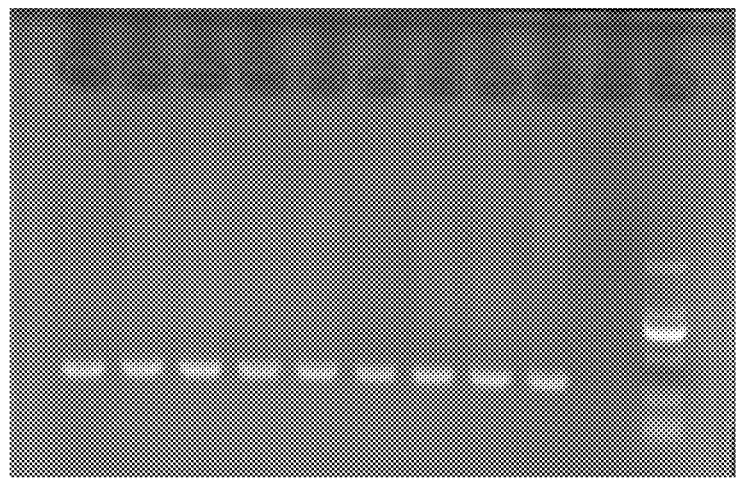
FIG. 1 shows the electrophoresis testing results of PCR agarose gel for three genotypes.

Unless otherwise specified, the experimental methods used in the following embodiments are all conventional ones.

Unless otherwise specified, the materials and reagents used in the following embodiments are all commercially available.

The wing vein blood sampling and phenol imitation methods used in the following embodiments are all routine operations in the art.

Red feather means all chicken feathers are red.

Embodiment 1: Primer Required for the Method for Identifying the Red Feather Causative Mutation Genotypes of White Leghorn Chickens and Establishment of the Method I. Discovery of the Red Feather Mutation Sites in White Leghorn Chickens 1. Extracting the Genomic DNA of the Chickens to be Tested The 2,000 white leghorn hens from Beijing Huadu Yukou Poultry Industry Co., Ltd. were cross bred with Rhode Island Red roosters. The feather color phenotypes of the offspring through hybridization were counted. Nine white leghorn hens that had more than five offspring hens and all such offspring hens had red feathers were selected as the red feather group, while nine white leghorn hens that had more than five offspring hens and all such offspring hens had white feathers were selected as the white feather group. Both groups of hens were the chickens to be tested.

Blood was venously sampled from the wings of the chickens to be tested. Next, the sampled blood was anticoagulated with anticoagulants, lysed and digested with protease, and then genomic DNA was extracted with the phenol-chloroform method and dissolved in sterilized double-distilled water for subsequent use, thereby obtaining the DNA of each chicken in the red feather group and that in the white feather group.

2. Re-Sequencing

The genomic DNA of each chicken in the red feather group and that in the white feather group were re-sequenced using the Illumina HiSeq 4000 sequencer.

Data analysis was conducted on the re-sequenced data and the specific analysis procedures are as follows:

1) The NGS QC Toolkit was used to control the quality of the original reads, remove the reads that has lower quality and contains adaptors or primers.

2) The Burrows Wheeler Aligner (BWA) software was used to compare the reads after quality control to the galGal4 reference genome.

3) The Picard software was used to mark and delete PCR duplicates.

4) SAMtools was used to conduct statistics on the comparison results of the two DNA libraries of each individual to obtain the final comparison result of this individual.

5) The GATK software was used to perform SNP calling on sequencing data and perform fixed index analysis (Fst) based on SNP polymorphism to determine the significant difference interval between the two groups.

6) The SNP in the significant difference interval was verified to determine the molecular marker of the causative mutation SNP of the red feather of the white leghorn breed, which was named as red feather SNP.

This red feather SNP site is the 18,288,303rd deoxynucleotide in the positive-sense strand of the 11th chromosome, as shown in the sequence information of the chicken reference genome Gallus_gallus-4.0 version published in NCBI, and it is also at Position 253 of SEQ ID NO: 1. Besides, the nucleotide of the red feather SNP site is A or G and its genotypes are AA, GG or AG.

The red feather SNP site is on the autosome.

II. Design and Synthesis of Amplification Primers for the Red Feather SNP Sites of White Leghorn Chickens The primer with a digested site was designed based on the red feather SNP position information found above, and synthesized by Shenzhen Huada Genomics Technology Service Co., Ltd.

```
Forward primer F:
                                        (SEQ ID NO: 2)
5'-GCCGCCATCCTCAAGAACA-3'

Reverse primer R:
                                        (SEQ ID NO: 3)
5'-AAAAAAAAAAAAAAAACGCAGCGCATAGAAGATCG-3'.
```

III. Establishment of the Method for Identifying the Red Feather Causative Mutation Genotypes of the White Leghorn Chickens to be Tested with the Restriction Fragment Length Polymorphism 1. The Genomic DNA of the White Leghorn Chickens to be Tested with GG, GA and AA Genotypes Verified Through Sequencing and Hybridization Experiments was Extracted.

2. PCR Amplification

The genomic DNA of the white leghorn chickens to be tested obtained based on the above 1 was used as a template, and the PCR amplification using the forward primer F and the reverse primer R designed in the above II was used to obtain a PCR amplification product (SEQ ID NO: 1).

The above 20 μL PCR amplification system is as follows:

| 2*PCR Mix (Beijing TransGen Biotech Co., Ltd., AS111-03) | 10 μL; |
| --- | --- |
| ddH2O | 7.7 μL; |
| Forward primer F | 0.4 μL; |
| Forward primer R | 0.4 μL; |
| DNA template | 1.5 μL. |

The above PCR reaction procedures are as follows:

| ① 94° C. | 5 min |
| --- | --- |
| ② 94° C. | 30 sec |
| ③ 52.5° C. | 30 sec |
| ④ 72° C. | 30 sec |
| ⑤ Goto ② for 32 cycles | |
| ⑥ 72° C. | 10 min |
| ⑦ Stored at 4° C. | |

Agarose gel testing: 1.5~2% agarose gel was used for testing, the voltage was 100V, and the electrophoresis duration was 35 minutes.

The results are shown in FIG. 1. The PCR products were all 288 bp (SEQ ID NO: 1); the Marker was DM2000, which was 100 bp, 250 bp, 500 bp, 750 bp, 1,000 bp and 2,000 bp from bottom to top.

3. Digestion

The above PCR amplified products were digested with NruI endonuclease to obtain the digestion product.

The digestion system is as follows:

| 10 μL system: | |
| --- | --- |
| NruI endonuclease | 0.5 μL |
| Buffer | 1 μL |
| PCR product | 4 μL |
| ddH$_2$O | 4.5 μL |

Digestion reaction procedures:

| ① 37° C. | 1 h |
| --- | --- |
| ② Stored at 4° C. | |

The above digestion products were tested using 1.5-2% agarose gel, the voltage was 100V, and the electrophoresis time was 35 minutes.

Figure 2:
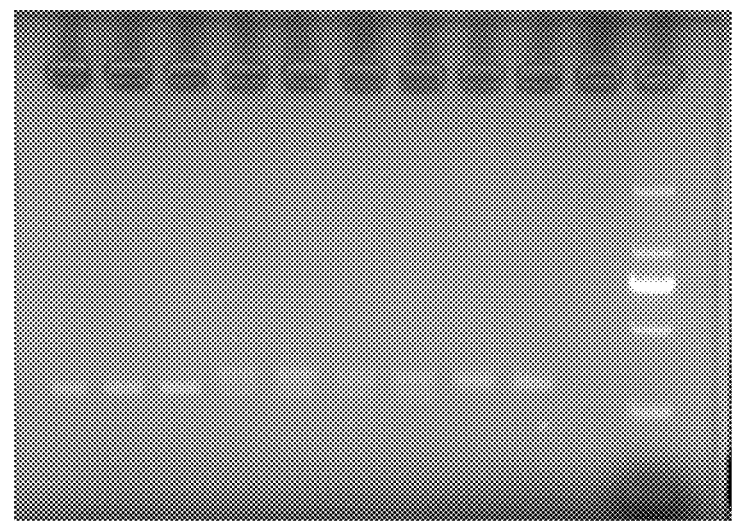
FIG. 2 shows the electrophoresis testing results of digested agarose gel for three genotypes.

The results are shown in FIG. 2. The individuals with GG genotype in Lanes 1, 2, and 3 showed one band of 253 bp after being digested with NruI endonuclease; the individuals with GA genotype in Lanes 4, 5, 6, and 7 showed two bands of 288 bp and 253 bp after being digested with digested NruI endonuclease; and the individuals with AA genotype in Lanes 8 and 9 showed one band of 288 bp after being digested with NruI endonuclease. The Marker was DM2000, which included 100 bp, 250 bp, 500 bp, 750 bp, 1,000 bp and 2,000 bp from bottom to top.

It can be seen that:

The digestion products of the white leghorn chickens with GG genotype had only one 253 bp band (some chickens of this group were in Lanes 1-3). In the genome of this group of white leghorn chickens, the genomes at the red feather SNP site were all GG (obtained by sequencing and verified by cross-breeding), so the chickens were homozygous gene individuals with red feathers, namely, 100% of the offspring hens obtained by cross breeding this group of chickens with Rhode Island Red roosters had red feathers; after sequenced, the 253 bp digestion product was the 1-253 bp in SEQ ID NO: 1;

The digestion products of the white leghorn chickens with AA genotype had only 288 bp band (some chickens of this group were in Lanes 8 and 9). In the genome of this group of white leghorn chickens, the genomes at the red feather SNP site were all AA (obtained by sequencing and verified by cross-breeding), so the chickens were non-homozygous gene individuals with red feathers, namely, 100% of the offspring hens obtained by cross breeding this group of chickens with Rhode Island Red roosters had no red feathers; after being sequenced, the 288 bp digestion product was the 1-288 bp in SEQ ID NO: 1;

The digestion products of the white leghorn chickens with GA genotype had two bands, i.e. 288 bp and 253 bp (some chickens of this group were in Lanes 4-7). In the genome of this group of white leghorn chickens, the genomes at the red feather SNP site were all GA (obtained by sequencing), so the chickens were heterozygosis gene individuals with red feathers, namely, the offspring hens obtained by cross-breeding this group of chickens with Rhode Island Red roosters consist of the ones with red feathers and the ones without red feathers. After being sequenced, the 288 bp digestion product was the 1-288 bp in SEQ ID NO: 1; and the 253 bp digestion product was the 1-253 bp in SEQ ID NO: 1;

Therefore, the above method can be used to identify the red feather causative mutation genotypes of the white leghorn chickens to be tested or to test the red feather traits of the hybrid offspring hens of the white leghorn chickens to be tested and Rhode Island Red roosters. The specific steps are as follows:

1. The genomic DNA of the white leghorn chickens to be tested was extracted.
2. The PCR amplification was performed with the above two primers to obtain the PCR amplification products;
3. The PCR amplification products were digested with NruI to obtain the digestion products.

The size of the digestion products was tested:

If the size of the digestion product of the white leghorn chickens to be tested is only 253 bp, then such chickens are the ones with the red feather causative mutation homozygous genotype (in the genome of this group of white leghorn chickens, the genome at the red feather SNP site is GG) and the hybrid offspring hens of these white leghorn hens and Rhode Island Red roosters will have only red feather traits;

If the size of the digestion product of the white leghorn chickens to be tested is only 288 bp, then such chickens are the ones with the red feather causative mutation homozygous genotype (in the genome of this group of white leghorn chickens and the genome at the red feather SNP site is AA), and the hybrid offspring hens of these white leghorn hens and Rhode Island Red roosters will have no red feather traits;

If the size of the digestion products of the white leghorn chickens to be tested is 288 bp and 253 bp, then such chickens are the ones with the red feather causative mutation heterozygosis genotype (in the genome of this group of white leghorn chickens and the genome at the red feather SNP site is AG), and the hybrid offspring hens of these white leghorn hens and the Rhode Island Red roosters will have red and non-red feather traits.

The red feather causative mutation genotype is the red feather causative mutation homozygous or heterozygous genotype:

The said red feather causative mutation homozygous genotype is the GG genotype at the red feather SNP site in the genome, and the hybrid offspring hens of the white leghorn hens with the red feather causative mutation homozygous genotype and the Rhode Island Red roosters will have only red feather traits;

The said red feather causative mutation heterozygosis genotype is the AG genotype at the red feather SNP site in the genome, and the hybrid offspring hens of the white leghorn hens with the red feather causative mutation heterozygosis genotype and the Rhode Island Red roosters will have red and non-red feather traits;

The said non-red feather causative mutation genotype is the AG genotype at the red feather SNP site in the genome, and the hybrid offspring hens of the white leghorn hens with the non-red feather causative mutation genotype and the Rhode Island Red roosters will only have non-red feather traits.

Embodiment 2: Breeding of the Female Parent of the White Leghorn Chickens with the Red Feather Homozygous Causative Mutation Genotype and Establishment of Commercial Strains of Red Feather Pink-Shell Laying Hens I. Breeding of the Female Parent of the White Leghorn Chickens with the Red Feather Homozygous Causative Mutation Genotype 1. Extraction of Genomic DNA The genomic DNA of 1,573 white leghorn chickens to be tested was extracted.

2. PCR Amplification

The genomic DNAs of 1,573 white leghorn chickens to be tested were respectively used as a template to perform PCR amplification according to Step 2 in the above III of Embodiment 1 to obtain the PCR amplification products.

3. Digestion

The above PCR amplification products were digested with NruI to obtain the digestion products.

Testing the size of the digestion products:

If the size of the digestion product of the white leghorn chickens to be tested is only 253 bp, then such chickens are the ones with the red feather causative mutation homozygous genotype and the hybrid offspring hens of the white leghorn hens and the Rhode Island Red roosters will only have red feather traits;

If the size of the digestion product of the white leghorn chickens to be tested is only 288 bp, then such chickens are the ones with the red feather causative mutation homozygous genotype, and all the hybrid offspring hens of these white leghorn hens and the Rhode Island Red roosters will have no red feather traits;

If the size of the digestion product of the white leghorn chickens to be tested is 288 bp and 253 bp, then such chickens are the ones with the red feather causative mutation heterozygosis genotype and the hybrid offspring hens of these white leghorn hens and the Rhode Island Red roosters will have red and non-red feather traits.

The results are as below:

Among the 1,573 white leghorn hens tested, the size of the digested products of 962 hens was only 253 bp, so these hens were judged to be red feather causative mutation homozygous genotype individuals, and the hybrid offspring hens of these hens and the Rhode Island Red roosters will have red feathers;

Among the 1,573 white leghorn hens tested, the size of the digested products of 19 hens was only 253 bp, so these hens were judged to be non-red feather causative mutation homozygous genotype individuals, and the hybrid offspring hens of these hens and the Rhode Island Red roosters will have no red feathers;

Among the 1,573 white leghorn hens tested, the size of the digested products of 592 hens was 288 bp and 253 bp, so these hens were judged to be red feather causative mutation heterozygosis genotype individuals, and the hybrid offspring hens of these hens and the Rhode Island Red roosters include the ones with red feathers and the ones without red feathers;

Experimental verification:

The 962 individuals with the red feather causative mutation homozygous genotype as the female parent were cross bred with Rhode Island Red roosters. According to the testing result, all the obtained 3,620 offspring hens had red feathers.

The 592 individuals with the red feather causative mutation heterozygous genotype as the female parent were cross bred with the Rhode Island Red roosters. According to the testing result, among the obtained 2,257 offspring hens, 1,182 hens had red feathers and 1,075 hens had no red feathers.

The 19 non-red feather causative mutation individuals in the above SNP identification as the female parent were cross bred with the Rhode Island Red roosters. According to the testing result, among the 61 offspring hens obtained, no hens had red feathers and 61 hens had non-red feathers.

It can be seen that the above cross breeding results are consistent with the identification results of the method of the present invention. Therefore, the primer and method of the present invention can be used to identify the red feather causative mutation genotypes of white leghorn chickens, and to judge the feather color traits of the hybrid chickens of the white leghorn chicken and the Rhode Island Red roosters.

II. Establishment of Commercial Strains of Red Feather Pink-Shell Laying Hens

The white leghorn chickens with the GG genotype were cross-bred with the Rhode Island Red roosters. The offspring hens were all red feathers, and all the offspring little roosters had no red feathers, thus enabling the establishment of commercial strains of red feather pink-shell laying hens.

III. Application of White Leghorn Chickens with the Red Feather Causative Mutation Homozygous or Heterozygous Genotype The red feather SNP site is on the autosome, so the method in the above II can also be used to identify the red feather causative mutation genotypes of the full-sib white leghorn chickens with GG and GA genotypes, and the white leghorn roosters with GG genotype were selected for subsequent use.

The white leghorn roosters with GG genotype were subject to expanded propagation and breeding with all the white leghorn individual hens with GG genotype. After four generations of breeding, the pure lines of white leghorn chickens with red feather causative mutation genotypes were obtained. The red feather SNP site genotype was GG type.

The present invention discloses a method for breeding the commercial strains of red feather pink-shell laying hens. It provides a primer pair for identifying the red feather causative mutation homozygous genotype of white leghorn chickens, which is composed of the single-stranded DNA molecule shown in SEQ ID NO: 2 of the Sequence List and the single-stranded DNA molecule shown in SEQ ID NO: 3 of the list. After the primer was designed according to the upstream and downstream nucleotide sequences of the 18,288,303$^{rd}$ deoxynucleotide in the positive-sense strand of the 11$^{th}$ chromosome as shown in the sequence information of the chicken reference genome Gallus_gallus-4.0 version published in NCBI, the genotype (SNP) at this site is tested through the restriction fragment length polymorphism, the genotype of the site (SNP) was tested through the restriction fragment length polymorphism; the offspring hens obtained by cross breeding the homogenous female parent (the homogenous female parent was obtained through expanded propagation of the white leghorn chickens with the red feather causative mutation homozygous genotype) and the Rhode Island Red rooster as a male parent are all of red feather phenotype, meeting the market demands and enjoying a broad prospect for promotion.

What is claimed is:

1. A primer pair for identifying red feather causative mutation genotypes of white leghorn chickens, which is composed of the single-stranded DNA molecule shown in SEQ ID NO: 2 and the single-stranded DNA molecule shown in SEQ ID NO: 3.

2. A kit for identifying the red feather causative mutation genotypes of white leghorn chickens, comprising the primer pair according to claim 1 and a restriction endonuclease which is NruI.

3. A method comprising:
determining red feather causative mutation genotypes of white leghorn chickens by performing PCR on the white leghorn chickens using a primer pair which is composed of the single-stranded DNA molecule shown in SEQ ID NO: 2 and the single-stranded DNA molecule shown in SEQ ID NO: 3;
and performing one or more of:
breeding the white leghorn chickens with the red feather causative mutation genotypes, which are homozygous or heterozygous;
breeding the white leghorn chickens, that when hybridized with Rhode Island Red roosters, produce hybrid offspring hens having red feathers;
identifying red feather traits of hybrid offspring hens;
or establishing commercial strains of red feather pink-shell laying hens.

4. A method for identifying red feather causative mutation genotypes of white leghorn chickens to be tested, the method comprising:
1) performing PCR amplification on the white leghorn chickens to be tested using the primer pair of claim 2 to obtain a PCR amplification product;
2) digesting the PCR amplification product with the restriction endonuclease of claim 2 to obtain a digestion product;
3) testing the digestion product and identifying the red feather causative mutation genotypes of the white leghorn chickens to be tested according to a size of the digestion product.

5. The method according to claim 4, characterized in that: the red feather causative mutation genotypes of the white leghorn chickens to be tested are as follows:
if the size of the digestion product of the white leghorn chickens to be tested is only 253 bp, then such chickens are the ones with a red feather causative mutation homozygous genotype;
if the size of the digestion product of the white leghorn chickens to be tested is 288 bp and 253 bp, then such chickens are the ones with a red feather causative mutation heterozygous genotype.

6. The method according to claim 4, characterized in that: a template for the PCR amplification is genomic DNA of the white leghorn chickens to be tested.

7. A method for breeding white leghorn chickens with the red feather causative mutation homozygous genotype, comprising:
1) determining the red feather causative mutation genotype of one or more while leghorn chickens according to claim 5; and
2) breeding the white leghorn chickens of step (1) which have a red feather causative mutation homozygous genotype.

8. A method for breeding commercial strains of red feather pink-shell laying hens, comprising:
1) determining the red feather causative mutation genotype of one or more white leghorn chickens according to claim 5;
2) breeding the white leghorn chickens of step (1) which have a red feather causative mutation homozygous genotype to obtain homogenous white leghorn chickens with the red feather causative mutation homozygous genotype; and
3) cross-breeding the homogenous white leghorn chickens with the red feather causative mutation homozygous genotype of step 2) as female parents and Rhode Island Red roosters as male parents to thereby obtain the commercial strains of red feather pink-shell laying hens.

9. A method for identifying red feather traits of hybrid offspring hens of white leghorn chickens and Rhode Island Red roosters, including the following steps:
1) performing PCR amplification on white leghorn chickens to be tested using the primer pair of claim 2 to obtain a PCR amplification product;
2) digesting the PCR amplification product with the restriction endonuclease of claim 2 to obtain a digestion product; and 3) detecting the digestion product and identifying the red feather traits of the hybrid offspring hens of the white leghorn chickens and the Rhode Island Red roosters according to a size of the digested product.

10. The method according to claim 9, characterized in that: the red feather traits of the hybrid offspring hens of the white leghorn chickens and the Rhode Island Red roosters according to the size of the digestion product are as follows:

if the size of the digestion product of the white leghorn chickens to be tested is only 253 bp, then all the hybrid offspring hens of such white leghorn chickens as female parents and the Rhode Island Red roosters as male parents are the ones with red feather traits;

if the size of the digestion product of the white leghorn chickens to be tested is only 288 bp, then all the hybrid offspring hens of such white leghorn chickens as female parents and the Rhode Island Red roosters as male parents are the ones without red feather traits;

if the size of the digestion product of the white leghorn chickens to be tested is 288 bp and 253 bp, then the hybrid offspring hens of such white leghorn chickens as female parents and the Rhode Island Red roosters as male parents include ones with and without red feather traits.

* * * * *